United States Patent [19]

McCormick et al.

[11] Patent Number: 4,496,724

[45] Date of Patent: Jan. 29, 1985

[54] CONTROLLED RELEASE PESTICIDES

[76] Inventors: Charles L. McCormick, 2308 Clayton Pl.; Kenneth W. Anderson, 3406 Campbell Dr., both of Hattiesburg, Miss. 39401

[21] Appl. No.: 452,385

[22] Filed: Dec. 22, 1982

[51] Int. Cl.$^3$ .......................................... C07D 253/06
[52] U.S. Cl. .................................................... 544/182
[58] Field of Search ......................................... 544/182

[56] References Cited

PUBLICATIONS

Morrison and Boyd, Organic Chemistry, 2nd ed., pp. 926–927, (1966).
Fuson, Reactions of Organic Compounds, p. 337 (1964).

*Primary Examiner*—John M. Ford
*Attorney, Agent, or Firm*—Quarles & Brady

[57] ABSTRACT

Controlled release pesticide-polymers are prepared by reacting a polymer having a pendant group containing a reactive hydrogen with a chloroformamide derivative of a pesticide. In a preferred embodiment, metribuzin chloroformamide is prepared by reacting metribuzin with phosgene at a temperature of about 40° C. The metribuzin chloroformamide is then reacted with cellulose to form a pesticide-polymer from which the metribuzin is released under use conditions by hydrolytic degradation of the carbamate bond attaching the metribuzin to the polymer.

3 Claims, No Drawings

CONTROLLED RELEASE PESTICIDES

FIELD OF THE INVENTION

The present invention relates to controlled release pesticide-polymers which are prepared by reacting a polymer having pendant groups containing a reactive hydrogen with a pesticide derivative. More particularly, it relates to a novel method of preparing pesticide derivatives to be used in preparing the pesticide-polymers.

BACKGROUND OF THE INVENTION

In my earlier U.S. Pat. No. 4,267,281, I disclosed the preparation of controlled release pesticide-polymers by reacting a polymer having pendant groups containing a reactive hydrogen with an isocyanate derivative of a pesticide. The isocyanate derivatives described in that patent were prepared by reacting an amino containing pesticide with phosgene under suitable reaction conditions as described in the literature. (See R. Morrison and R. Boyd, *Organic Chemistry*, 2nd Ed. 1966, pp. 926–927 and R. Fuson, *Reactions of Organic Compounds*, 1964, p. 337). The patent also disclosed that the isocyanate derivatives could be prepared from the corresponding amides using a Hoffman rearrangement. (See. D. Grant and G. Hammond, *Organic Chemistry*, 2nd Ed. 1964, pp. 90 and 304).

A pesticide of special interest and for which there could be extensive use in a controlled-release form is the pre- and post-emergence herbicide 4-amino-6-tert-butyl-3-(methylthio)-as-triazine-5(4H) one, which is commonly known as metribuzin.

It is difficult to prepare the isocyanate derivative of some pesticides, such as metribuzin, in good yields using prior art methods. When metribuzin and phosgene are reacted at temperatures of about 66° C., as suggested in the literature and my earlier patent, very little metribuzin isocyanate is produced. Reaction at higher temperature and/or in the presence of tertiary amines has no effect in increasing the yield of isocyanate and can lead to the production of competing products. The major products produced at those temperatures are the cyclic trimer, linear polyurets, or a mixture of the two, which are formed by competing reactions. Apparently, at temperatures of about 66° C. enough activation energy is present to cause further reaction of any metribuzin isocyanate which forms to yield the cyclic trimer and/or polyurets. The rate of such reactions competes with that of isocyanate formation. As a result, only a low, steady-state concentration of the isocyanate derivative is obtained.

There is a need for an improved method of preparing controlled release pesticide-polymers which does not require the use of isocyanate derivatives of pesticides, which derivatives may be difficult to obtain in good yields.

SUMMARY OF THE INVENTION

It is the general object of the present invention to disclose an improved method of preparing biodegradable, controlled release, pesticide-polymers.

It is a further object to disclose a novel method of preparing controlled released pesticide-polymers which comprises reacting the chloroformamide derivative of a pesticide with a polymer.

It is a still further object to disclose the preparation of metribuzin chloroformamide.

These and still other objects of the invention will be apparent to those skilled in the art from the disclosure which follows.

In the practice of the present invention, an amino containing pesticide, such as metribuzin, is reacted with phosgene under mild conditions (e.g., at about 42° C.) to give good yields of the chloroformamide derivative of the pesticide. When this derivative is reacted with a suitable polymer having a reactive hydrogen, such as cellulose, a pesticide-polymer is obtained having the pesticide pendantly attached through carbamate linkages to the polymer. The resulting pesticide-polymer is useful as a controlled-release preparation from which the pesticide is released by hydrolytic degradation of the carbamate bond.

The method of the present invention is particularly useful in preparing pesticide-polymers containing metribuzin because such pesticide-polymers cannot be prepared in good yields by prior art methods.

DESCRIPTION OF THE PREFERRED EMBODIMENT

In the preferred method of the invention, an amino group containing pesticide, such as metribuzin, is reacted with phosgene at mild conditions of about 42° C., until the reaction is complete (e.g., one to five hours) to obtain the chloroformamide derivative of the pesticide. The chloroformamide derivative is then reacted with a polymer having a reactive hydrogen, preferably at room temperature, to form the polymer-pesticide which can be isolated from the reaction mixture by conventional methods.

The preparation of the pesticide-chloroformamide is illustrated by the following diagram in which the pesticide is metribuzin:

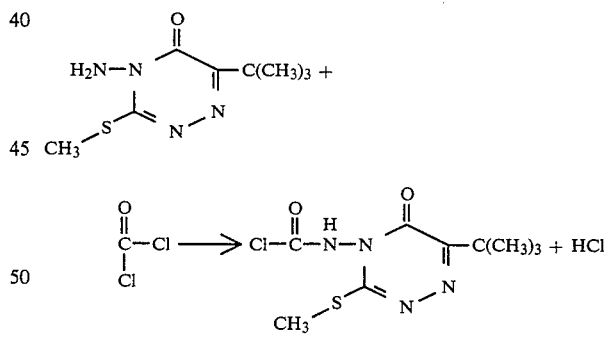

The term "pesticide" as employed herein is intended to cover any amino group containing material which is used for biologic control of unwanted organisms. It includes insecticides, fungicides, herbicides, nematocides and other biocides.

Representative of the pesticides especially preferred for use in the present invention are the following:
3-amino-5-triazole;
3-amino-2,5-dichlorobenzoic acid;
4-amino-3,5-6-trichloropicolinic acid;
5-amino-4-chloro-2-phenyl-3(2H)-pyridazinone;
2-amino-3-chloro-1,4-naphthoquinone;
4-amino pteroylglutamic acid;
3-amino-2,5-dichlorobenzoic acid;
4-amino-3,5,6-trichloropiodinic acid; and 4-amino-6-tert-butyl-3-(methylthio)as-triazine-5(4H) one, which is commonly known as metribuzin.

The novel pesticide-polymer systems of the present invention may be represented by the following formula:

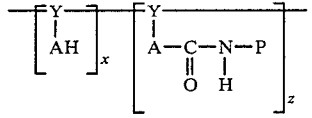

in which

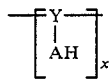

is the unreacted portion of a polymer of the formula

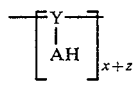

in which $x+z$ is from 5 to $1.0 \times 10^7$, x is less than $x+z$ and can be zero, A is the remainder of a reactive hydrogen containing pendant group of the formula AH from which the reactant hydrogen H has been removed. Although a single pendant AH group is shown, the repeating backbone of the polymer may contain up to 20 pendant groups and it is intended that AH be interpreted to include multiple groups. The extent of the reaction of the reactive hydrogen containing pendant groups of the polymer may range from about 1% to 100%. Representative of AH are such groups as —OH, —NH$_2$, —SH, —COOH, —CO$_3$H,

and —PO$_3$H. P is the pesticidal remainder of a pesticide of the formula P—NH$_2$ and Y represents the repeating structure of the macromolecular backbone of the polymer.

The preferred polymers for use in the present invention are the natural polysaccharides such as cellulose, chitin, and starch because they are biodegradable and readily available. Representative of other polymers having a reactive hydrogen which also may be used in the present invention are:
Polyvinyl Alcohol;
Polyvinyl Alcohol-polyvinyl acetate copolymers;
Polyacrylic Acid;
Polymethacrylic Acid;
Polyvinyl Amine; and
Cellulose derivatives such as:
  (1) hydroxy methyl cellulose,
  (2) hydroxy ethyl cellulose,
  (3) hydroxy propyl cellulose,
  (4) carboxymethyl cellulose,
  (5) xanthate derivatives of cellulose
  (6) and other hydroxy-substituted polysaccharides such as dextrans, xylans, and pectins.

The preparation of the pesticide-polymer from the chloroformamide derivative of metribuzin and polyvinyl alcohol may be illustrated as follows:

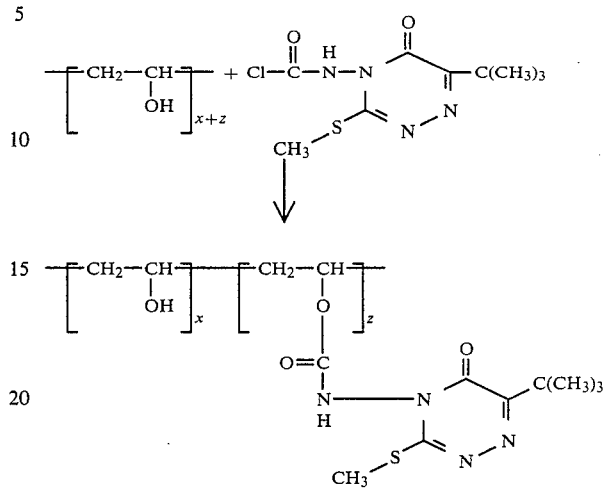

in which x and z are as previously defined.

Representative of other pesticide-polymer systems which can be obtained by exercise of the novel method of the present invention are those obtained by reacting the following:
4-chloroformamido-6-tert-butyl-3-(methylthio)-astriazine-5(4H) one and polyvinyl amine;
4-chloroformamido-6-tert-butyl-3-(methylthio)-astriazine-5(4H) one and chitin;
4-chloroformamido-6-tert-butyl-3-(methylthio)-astriazine-5(4H) one and a 1:1 copolymer of polyvinyl alcohol and polyvinyl acetate;
4-chloroformamido-6-tert-butyl-3-(methylthio)-astriazine-5(4H) one and dextran (average molecular weight 70,000);
3-chloroformamido-2,5-dichlorobenzoic acid and polyvinyl alcohol;
3-chloroformamido-2,5-dichlorobenzoic acid and cellulose;
3-chloroformamido-2,5-dichlorobenzoic acid and chitin;
3-chloroformamido-2,5-dichlorobenzoic acid and a 1:1 copolymer of polyvinyl alcohol and polyvinyl acetate;
3-chloroformamido-2,5-dichlorobenzoic acid and polyvinyl amine;
3-chloroformamido-2,5-dichlorobenzoic acid and dextran (average molecular weight 70,000).

It will be apparent to those skilled in the art that the present invention which utilizes the chloroformamide derivative of a pesticide as a reactant provides an alternative method of preparing the polymer-pesticides disclosed in my earlier U.S. Pat. No. 4,267,281.

The following examples are presented to illustrate the practice of the invention.

EXAMPLE 1

Preparation of Chloroformamide Derivative of Metribuzin

Phosgene was condensed in a jacketed addition funnel at $-50°$ C. until 90 ml (126 g, 1.27 mole) was collected. The phosgene was then slowly added with stirring to 200 ml of THF in a 1-liter, three-necked, round-bottomed flask at 0° C. The flask was vented through a partial take-off still head to scrubber solutions containing approximately 10 wt % ammonia in water. After the phosgene addition was completed, a solution of 25 g of metribuzin (0.117 mole) in 100 ml THF was added dropwise with stirring over a period of 50 minutes. The temperature of the mixture was held at 0° C. throughout this addition, and a fine, white precipitate was formed which remained suspended. The suspension was stirred an additional 30 minutes at 0° C. after completion of the metribuzin addition. A heating mantle was then placed on the flask and the temperature was slowly raised to 42° C. The solution became clear after about three hours, during which slight reflux was noted. After one additional hour, sufficient vacuum was applied through the scrubbing system to allow distillation of the excess phosgene/THF/HCl mixture. Care was taken to ensure that pressure fluctuations did not allow the scrubbing solutions to back-up into the reactor. The distillate temperature climbed from 25° C. to 40° C. over a period of one hour, during which approximately 200 ml of distillate was collected. Distillation was continued until approximately 125 ml of solution remained in the reactor; the temperature therein was never higher than 43° C. An infrared spectrum of the reaction mixture showed no phosgene absorption at 840 cm$^{-1}$, therefore the distillation was stopped. (Fresh THF may be added and distillation continued if phosgene removal is incomplete at this point.) The resulting product, which was a fairly concentrated solution of the chloroformamide in THF, was further concentrated on a rotary evaporator at room temperature to about 75 ml volume. The solution was viscous and slightly cloudy. The solution weight was 59.5 g. For purposes of Example 2, it was assumed that the theoretical yield of 32.3 g was obtained.

The IR spectrum of a concentrated solution of the product in THF, exhibited a very strong absorption centered at 1840 cm$^{-1}$ for the carbonyl groups of the chloroformamide group. No absorption corresponding to the cyclic trimer or polyuret was seen.

Heating the chloroformamide in THF at 66° C. caused a gradual decrease in the IR absorption at 1840 cm$^{-1}$, with a concomitant increase at 1770 cm$^{-1}$. This indicated that the chloroformamide was converted to the isocyanate and then immediately into the cyclic trimer or polyurets.

EXAMPLE 2

Reaction of Metribuzin Chloroformamide with Cellulose

Five grams of lithium chloride was dissolved in 100 ml of N,N-dimethylacetamide (DMAC) in a 250 ml, three-necked, round-bottomed flask under nitrogen. One gram of cellulose powder (18.5 millimoles hydroxyl) was added and the slurry heated to 150° C. for ten minutes, then cooled to room temperature to form a clear, viscous, light yellow solution. Thirty grams of the concentrated solution of metribuzin chloroformamide in THF from Example 1 (16.3 g, 58.9 millimoles, based on 100% yield) was added dropwise with stirring at room temperature over a period of 30 minutes. The reaction mixture, which remained homogeneous, was stirred for 24 hours at room temperature. The polymer was precipitated by addition to 1500 ml of methanol. The solid polymer was collected and redissolved in either acetone or THF and reprecipitated in methanol. The solid was then dissolved in THF and precipitated the final time in heptane. This product was dried in vacuum at 60° C. for 18 hours and stored in a dessicator over calcium sulfate. The yield after three precipitations was 0.85 g.

The pesticide polymer thus obtained contained about 1.6 molecules of metribuzin per glucose repeating unit corresponding to about 72 wt % herbicide as measured by elemental analysis. The polymer had the same structure as that prepared using the isocyanate derivative as described in U.S. Pat. No. 4,267,281. In other experiments, degrees of substitution up to 3.0 pesticide units per polymer unit have been achieved.

The degree of substitution was determined by measuring the UV absorbance of a solution of the substituted polymer in distilled THF at 295 nm, and then comparing to known concentrations of metribuzin in THF. This procedure assumes that all herbicide is attached, that there is no interference from any other substances, and that there is no change in the extinction coefficient of the metribuzin chromophore as a result of attachment. Since the polymer was reprecipitated three times, it is reasonable to assume the first two conditions are met. Also, since attachment is through the amine linkage and does not directly involve any of the conjugated double bonds of metribuzin, the extinction coefficient should remain fairly constant. Alternatively, elemental analysis may be used to determine the degree of substitution.

The IR spectrum of a film of the polymer cast from THF showed the expected absorptions of both components in addition to C=O stretching vibrations of the linkage at about 1770 cm$^{-1}$ and 1710 cm$^{-1}$. A model compound showed a similar pattern of absorption at 1750 cm$^{-1}$ and 1700 cm$^{-1}$. These separate absorption bands are probably due to either Fermi resonance or mechanical coupling.

Carbon-13 NMR also supported the expected structure and further indicated attachment in that the spin-lattice relaxation times of the metribuzin carbon atoms were reduced. In this example, the cellulose concentration was deliberately kept low, and an apparently large stoichiometric excess of metribuzin chloroformamide was used to assure sufficient material and achieve the highest substitution possible under the condition employed.

EXAMPLE 3

Reaction of Metribuzin Chloroformamide with Polyvinyl Alcohol

Metribuzin chloroformamide was reacted with polyvinyl alcohol in a manner similar to that described in Example 2 to obtain a metribuzin-polyvinyl alcohol polymer.

EXAMPLE 4

Reaction of Metribuzin Chloroformamide with Starch

Metribuzin chloroformamide was reacted with starch in a manner similar to that described in Example 2 to obtain a metribuzin-starch polymer.

EXAMPLE 5

Reaction of Metribuzin Chloroformamide with Dextran

Metribuzin chloroformamide was reacted with dextran in a manner similar to that described in Example 2 to obtain a metribuzin-dextran polymer.

In the practice of the present invention the temperature at which the reaction of the pesticide and phosgene is conducted is important. It appears that a minimum temperature of about 40° C. is required for the production of chloroformamide in high yield. At or above 40° C., the dissolution of the hydrochloride salt of metribuzin and subsequent deprotonation and reaction with phosgene proceeds at a convenient rate. Temperatures of 60° C. or more are to be avoided as the formation of undesirable compounds occurs at those temperatures. The range of temperatures which appears to be usable to obtain acceptable yields of the chloroformamide derivative are from about 40° C. to about 55° C.

The pesticide-polymers prepared by the method of the present invention are useful products which can be used in the same manner as conventional pesticides and they are described in U.S. Pat. No. 4,267,281, which is incorporated by reference herein. For example, the pesticide-polymers can be powdered, granulated and sprayed, dusted or otherwise applied to: (1) reduce environmental pollution by reducing pesticide mobility, (2) reduce the number of applications required during the growing season, and/or (3) result in enhanced agricultural production. The amount of the pesticide-polymer to be employed, of course, will be dependent upon a number of factors including the concentration of the pesticide, the rate at which the pesticide is released, the field conditions and the pest being controlled.

It will be readily apparent to those skilled in the art that a number of modifications and changes can be made without departing from the spirit and scope of the present invention. For example, although only the preparation of the chloroformamide derivative of metribuzin has been described it will be apparent to those skilled in the art that the inventive method may be used to prepare the chloroformamide derivative of other pesticides, if desired. Therefore, it is not intended that the invention be limited by the illustrative examples, but only by the claims which follow.

We claim:

1. A method of preparing a pesticide derivative useful in the preparation of controlled release pesticide-polymers which comprise treating a pesticide having an amino group with phosgene at a temperature of about 40° C. to about 55° C. to form a chloroformamide derivative of the pesticide.

2. The method of claim 1 in which the pesticide is metribuzin.

3. Metribuzin chloroformamide.

* * * * *